US007588539B2

(12) United States Patent
Petersen

(10) Patent No.: US 7,588,539 B2
(45) Date of Patent: Sep. 15, 2009

(54) INTEGRATED LOW-POWER PW/CW TRANSMITTER

(75) Inventor: David A. Petersen, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 789 days.

(21) Appl. No.: 11/039,006

(22) Filed: Jan. 19, 2005

(65) Prior Publication Data

US 2005/0171431 A1 Aug. 4, 2005

Related U.S. Application Data

(60) Provisional application No. 60/538,449, filed on Jan. 21, 2004.

(51) Int. Cl.
*A61B 8/00* (2006.01)

(52) U.S. Cl. ....................................... 600/459; 327/382

(58) Field of Classification Search ................. 600/437, 600/459, 439, 447, 441, 446; 327/382; 73/609, 73/625

See application file for complete search history.

(56) References Cited

U.S. PATENT DOCUMENTS 6,028,484 A 2/2000 Cole et al.
6,572,546 B1 6/2003 Bax et al.
6,956,426 B2 * 10/2005 Wodnicki .................. 327/382
2003/0158478 A1 8/2003 Petersen et al.
2003/0176787 A1 * 9/2003 Gilbert et al. ............... 600/437
2004/0000841 A1 1/2004 Phelps et al.
2004/0002435 A1 1/2004 Petersen et al.
2005/0154300 A1 * 7/2005 Wodnicki et al. ........... 600/437
2005/0203391 A1 9/2005 Phelps

* cited by examiner

*Primary Examiner*—Eric F Winakur
*Assistant Examiner*—Lawrence N Laryea

(57) ABSTRACT

Integrated circuit transmitters allow for ultrasound imaging with both pulsed and continuous waves. High voltage and low voltage switches are integrated onto a same semiconductor chip. The high voltage switches are used for pulsed wave operation, and the low voltage switches are used for continuous wave operation. Power dissipation may be reduced by using low voltage circuits for the continuous wave operation. Both the pulsed and continuous waveforms are output on a common output from the integrated circuit. For continuous wave operation, one or more of the high voltage switches is used to provide a low resistance path to the common output or ground. For pulsed wave operation, one or more of the low voltage switches is used to provide a low resistance path to a common output or ground. A switch used for generating waveforms is also used for forming a low resistance path.

26 Claims, 2 Drawing Sheets

| EN | MODE | P | M1 STATE | M2 STATE | M3 STATE | M4 STATE | PULSER OUTPUT STATE |
|---|---|---|---|---|---|---|---|
| 0 | X | X | OFF | ON | OFF | ON | POWER-DOWN, Q=Vss(0V) |
| 1 | 0 | 0 | OFF | ON | OFF | ON | PW MODE, Q=Vss(0V) |
| 1 | 0 | 1 | ON | OFF | OFF | ON | PW MODE, Q=Vpp(20-200V) |
| 1 | 1 | 0 | OFF | ON | OFF | ON | CW MODE, Q=Vss(0V) |
| 1 | 1 | 1 | OFF | ON | ON | OFF | CW MODE, Q=VTXCW(2.5-12V) |

INTEGRATED LOW-POWER PW/CW TRANSMITTER

REFERENCE TO RELATED APPLICATIONS

The present patent document claims the benefit of the filing date pursuant to 35 U.S.C. §119(e) of Provisional U.S. Patent Application Ser. No. 60/538,449, filed Jan. 21, 2004, which is hereby incorporated by reference.

BACKGROUND

The present invention relates to ultrasound transmitters. In particular, a transmitter is operable for both pulsed wave and continuous wave modes.

Ultrasound transmitters include waveform generators for generating different types of waveforms. Pulsed waveforms are relatively high voltage waveforms, such as 20-200 volt peak amplitude, of short duration, such as one to three cycles. Unipolar or bipolar pulsed waves may be generated using one or more transistors. The transistors are switched on and off, connecting a high voltage sources (±) or ground to an output. For continuous wave operation, a multi-cycle waveform, such as ten or more cycles (e.g., generating MHz waveforms for minutes), with relatively lower voltage, such as 2.5 to 12 volts, is generated. Transistors for operating at high voltages inefficiently operate at lower voltages.

Many ultrasound systems use separate circuits for generating pulsed and continuous waves. Separate circuits are provided in different application specific integrated circuits, chips or even boards. The low voltage circuitry for continuous wave operation is not subjected to the high voltages of the pulsed waves.

Where space, power availability or heat dissipation restrictions exist, sacrifices in the types of waves transmitted may result. For example, transmitters integrated into a multi-dimensional transducer array housing have been developed to provide pulsed waveform generation. However, efficient continuous wave operation is still desired even for real-time three-dimensional imaging provided by multi-dimensional arrays with integrated transmitters.

BRIEF SUMMARY

By way of introduction, the preferred embodiments described below include methods and systems for ultrasound imaging with both pulsed and continuous waves. High voltage and low voltage switches are integrated onto a same semiconductor chip. The high voltage switches are used for pulsed wave operation, and the low voltage switches are used for continuous wave operation. Power dissipation may be reduced by using low voltage circuits for the continuous wave operation. Both the pulsed and continuous waveforms are output on a common output from the integrated circuit. For continuous wave operation, one or more of the high voltage switches is used to provide a low resistance path to the common output or ground. For pulsed wave operation, one or more of the low voltage switches is used to provide a low resistance path to a common output or ground. A switch used for generating waveforms is also used for forming a low resistance path.

In a first aspect, a transmitter is provided for ultrasound imaging with pulsed and continuous wave operation. The transmitter is improved by having high and low voltage switches integrated on a same circuit and having a common waveform output for the circuit.

In a second aspect, a waveform generator is provided for ultrasound imaging. At least a first higher voltage switch is integrated on a chip. At least a first lower voltage switch is also integrated on the chip with the first higher voltage switch. An output is provided on the chip. The output is connected with the first higher voltage switch and the first lower voltage switch.

In a third aspect, a method is provided for generating a transmit waveform as either of pulsed and continuous waves. Pulse waves are generated with high voltage switches in an integrated circuit. Continuous waves are generated with low voltage switches in the integrated circuit. A low or zero voltage is connected to at least one of the high voltage switches with at least one of the low voltage switches during generation of pulsed waves. The pulsed waves, when generated, and the continuous waves, when generated, are output on a common output from the integrated circuit.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

While high voltage switches used for pulsed wave generation may be used to also generate continuous waves, such use is inefficient and results in high power dissipation. Where power dissipation is a concern, such as in transmitters integrated within a transducer handle, high voltage switches may be undesirable for low voltage continuous wave operation. By integrating a low voltage pulser with a high voltage pulser, both pulsed and continuous wave operation is provided with more limited power dissipation. The high voltage and low voltage switches, such as field effect transistors, are integrated within a same application specific integrated circuit. The common waveform output for both the pulsed and continuous wave pulses provides further integration. During pulse wave operation, low voltage switches are maintained in a steady state. For continuous wave operation, the high voltage switches are maintained in a steady state. One high voltage switch is used for routing the continuous wave to the common output during continuous wave operation. The low voltage pulser is protected from high voltage exposure. During pulsed wave operation, one of the low voltage switches is used for forming a low resistance path to a ground or other steady state voltage.

Figure 1:
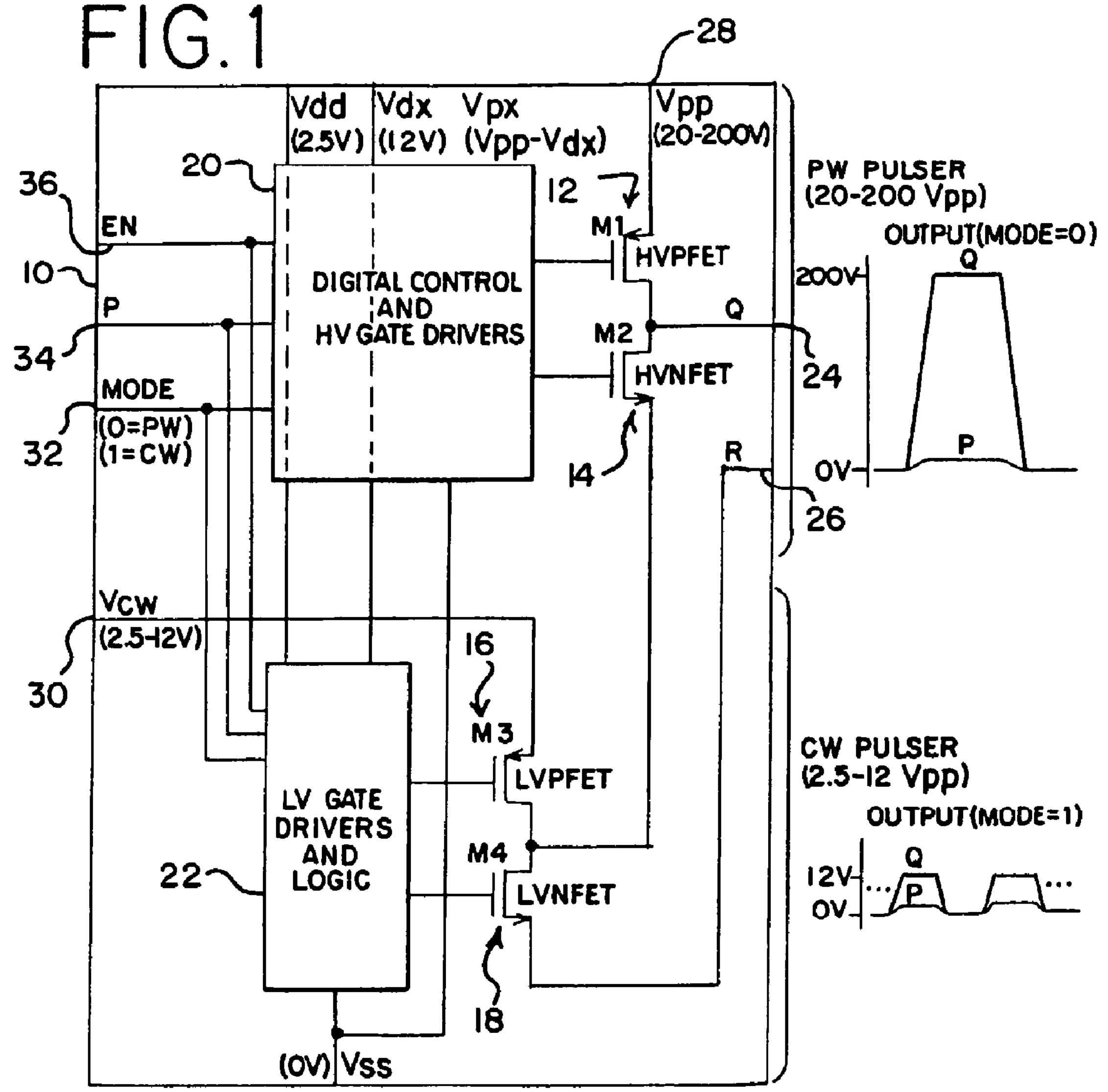
FIG. 1 is a circuit diagram of one embodiment of a integrated circuit for ultrasound imaging.

FIG. 1 shows one embodiment of a transmitter with a waveform generator for ultrasound imaging. The transmitter generates waveforms for both pulsed and continuous wave operation. The waveform generator and transmitter are integrated in a same circuit or chip 10. For example, an application specific integrated circuit 10 having one or more of the transmitters shown in FIG. 1 is provided. The different components and waveform generators are formed using the same or different processes on the same semiconductor substrate, such as using CMOS processes.

The integrated circuit 10 includes high voltage switches 12, 14, low voltage switches 16, 18, controller (high voltage gate driver) 20, controller (low voltage gate driver) 22, a common output 24, a ground, return line or other low impedance point connector 26, a high voltage power supply connector 28, a low voltage power supply connector 30, a mode input 32, a pulse timing input 34, and an enable input 36. Additional, different or fewer components may be provided. For example, additional high voltage or low voltage switches are provided. As another example, the controllers 20, 22 are formed as a single controller. As another example, an oscillator is included within the integrated circuit 10 for providing the timing information without a separate timing input 34. As yet another example, a single voltage connector is provided and divided or otherwise reduced to provide different voltages within the integrated circuit 10. As yet another example, additional inputs are provided for operating the controllers 20, 22 and/or the switches 12-18.

The integrated circuit 10 is operable to generate either pulsed or continuous waves. The common output 24 connects directly or indirectly with a transducer element for converting the generated waveform into acoustic energy. In the embodiment shown in FIG. 1, the continuous or pulsed waveforms are unipolar waveforms, but bipolar or more complex waveforms may be generated for either or both of continuous or pulsed wave operation.

The high voltage switches 12, 14 form a waveform generator and are complimentary field effect transistors, but may include other types of transistors or switches. Each of the high voltage switches 12, 14 may be of a same or different type of switch. Each high voltage switch 12, 14 has a turn-on threshold greater than 6 volts, such as being a 7 to 8 volt threshold. Greater or lesser threshold voltages may be provided. The high voltage switches 12, 14 are operable with at least 10 or more volts, such as allowing for a 10 to 200 volt supply at the input 28. A lower voltage may be provided, such as a voltage lower than the highest voltage for operating with continuous waves. For example, each of the high voltage switches 12, 14 is sized to have a gate oxide and other associated dimensions for operating with the 200 volt power supply. The drain-to-source resistance in the "on" state may be of any of various values, such as being 500 or less ohms. The high voltage switches 12, 14 are integrated on a same chip or within a same circuit.

The low voltage switches 16, 18 form a waveform generator and are complimentary field effect transistors, but other switches or transistors may be used. The low voltage switches 16, 18 may be of a same type or different type of switches from each other. Each low voltage switch 16, 18 has a turn-on threshold of less than 6 volts, such as a 1 to 2 volt threshold. Greater or lesser threshold voltages may be provided. The low voltage switches 16, 18 have a thinner oxide layer at the gate or other differences in dimensions for operation with exposure to a lesser voltage than the high voltage switches 12, 14. In one embodiment, the low voltage switches 16, 18 are smaller than the high voltage switches 12, 14. For example, the low voltage switches 16, 18 are operable with voltage supplies less than 10 volts, such as voltages input on the low voltage input 30 of 2.5 to 12 volts. The switching rate for the low voltage switches 16, 18 may be slower, the same or faster than the switching rate of the high voltage switches 12, 14. The drain-to-source resistance of the low voltage switches 16, 18, and the low voltage switch in 18 in particular, is much lower, such as ten times smaller than the drain to source resistance of the high voltage switch 14. For example, the resistance of the low voltage switches 16, 18 is 50 ohms or less. Lesser resistance is provided by having a smaller size. Greater resistances may be provided with a similar or different ratio of resistances from the high voltage switches 12, 14 to the low voltage switches 16, 18.

The low voltage switches 16, 18 are integrated on the same chip and associated circuit 10 as the high voltage switches 12, 14. The same semiconductor substrate is used for both the high voltage and low voltage switches 12-18.

The high voltage switch 12 connects between (a) the high voltage input 28 and (b) the common output 24 and other high voltage switch 14. During pulse wave operation, the high voltage switch 12 alternately connects and disconnects the common output 24 to the high voltage input 28. During continuous wave operation, the high voltage switch 12 is open to prevent high voltage at the input 28 from connection with the low voltage switches 16, 18 or common output 24.

The high voltage switch 14 connects between (a) the high voltage switch 12 and the common output 24 and (b) the low voltage switches 16, 18. During pulsed wave operation, the high voltage switch 14 alternately connects and disconnects the low voltage switches 16, 18 to the common output 24. The high voltage switch alternates opposite to the other high voltage switch 12. During continuous wave operation, the high voltage switch 14 is closed, providing a low resistance path from the low voltage switches 16, 18 to the common output 24.

The high voltage switches 12, 14 form a simple switching pulser. More complex pulsers may be provided using a greater number of switches. FIG. 1 shows a pulsed waveform as a single pulse generated by the high voltage switches 12, 14. A threshold voltage of 5 to 10 volts is used to turn on and off the high voltage switches 12, 14 for generating a pulsed waveform with a 10 to 200 volt peak amplitude. If the high voltage provided on a high voltage input 28 is reduced, such as for continuous wave operation, to a level used to drive the high voltage switches 12, 14, such as 12 volts shown by $V_{dx}$, the peak-to-peak voltage at the gates of the high voltage switches 12, 14 becomes comparable to the output voltage swing on the common output 24. This results in inefficient operation. By providing the low voltage switches 16, 18 operable in response to a lower gate or threshold voltage, more efficient continuous wave operation is provided.

The low voltage switch 16 connects between (a) the low voltage input 30 and (b) the high voltage switch 14 and the low voltage switch 18. During continuous wave operation, the low voltage switch 16 alternately connects and disconnects the low voltage on the low voltage input 30 to the common output 24 through the closed high voltage switch 14. During pulsed wave operation, the low voltage switch 16 is open. The low voltage input 30 is disconnected from the path from the high voltage switch 14 through the low voltage switch 18 to the ground or other voltage on the connection 26.

The low voltage switch 18 is connected between (a) the low voltage switch 16 and the high voltage switch 14 and (b) the connector 26. The connector 26 provides a ground or other output or input connection, such as a diode clipped substantially constant low voltage. For continuous wave operation, the low voltage switch 18 alternately connects and disconnects the connector 26 with the common output 24 through the high voltage switch 14. The low voltage switch 14 connects the ground or other limited voltage to the common output 24. The low voltage switch 18 alternates states opposite of the other low voltage switch 16. By alternating states, a continuous waveform extending from the ground or other voltage at the connector 26 with a peak voltage provided by the low voltage input 30 is generated as shown in FIG. 1. More complex pulsers with a greater number of switches may alternatively be provided. During pulsed wave operation, the low voltage switch 18 is closed, providing a low resistance path from the high voltage switch 14 to ground or other voltage provided at the connector 26.

Since the low voltage switches 16, 18 are integrated on the same semiconductor, an improved performance in power dissipation for continuous wave operation is provided. The lower threshold voltages of the low voltage switches 16, 18 require less peak-to-peak gate voltage to turn the switches 16, 18 on and off. As a result, less energy is required for each gate transition. Since the threshold voltage of the smaller low voltage switches 16, 18 is similar to or less than the peak voltage for the continuous wave forms, the low voltage pulser operates in an efficient manner. The high voltage circuitry, including the controller 20 and the high voltage switches 12, 14, are static during continuous wave operation, so do not contribute significantly to power dissipation except for parasitic capacitive loading effects.

The continuous and pulsed waveforms generated by the high voltage or low voltage switches 12-18 are output on the common output 24. The common output 24 is a signal trace, a connector, conductor or other device for electronically connecting the integrated circuit 10 on the semiconductor chip with external components. The common output 24 is connected with the two high voltage switches 12, 14 for receiving a pulsed wave. The common output 24 connects with the two low voltage switches 16, 18 through one of the high voltage switches 14 for receiving a continuous wave. In alternative embodiments, the common output 24 directly connects to one of the low voltage switches 16, 18, such as connecting to the high voltage and low voltage switches in parallel or connecting to the high voltage switches 12, 14 through one or more of the low voltage switches 16, 18. The common output 24 allows connection to a given ultrasound transducer element or other component without additional switching to select between the high voltage and low voltage pulsers integrated on the same circuit 10 or semiconductor chip.

The connector 26 is an input connection to ground in one embodiment. In other embodiments, a constant DC voltage other than zero volts is input. In yet other alternative embodiments, the connector 26 connects with receiver circuitry. Diodes are used to clip the positive and negative going voltages to a substantially low value, effectively grounding the connector 26 for operation of the high voltage and low voltage pulsers.

Figures 3, 4:
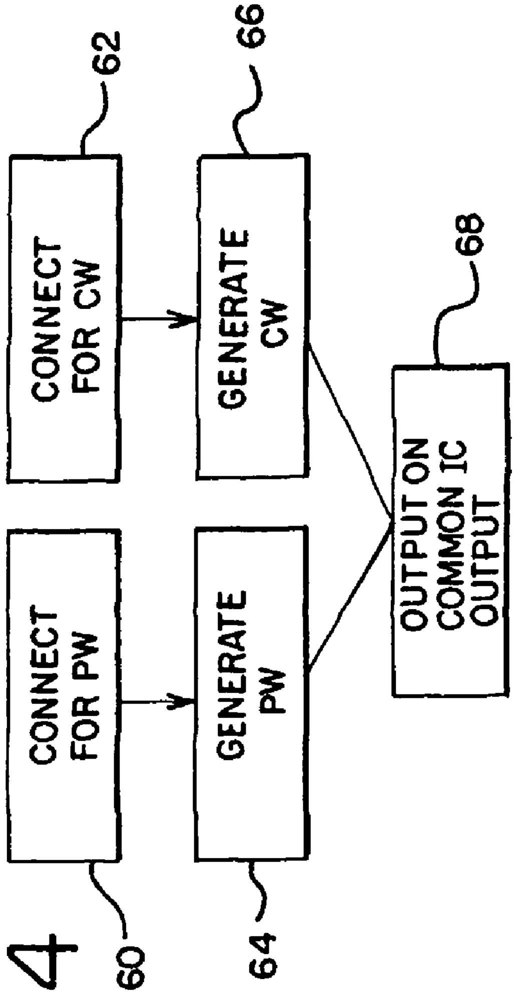
FIG. 3 is a table of one embodiment of the switch states for operation of the waveform generator of FIG. 1.
FIG. 4 is a flowchart diagram of one embodiment of a method for generating a transmit waveform as either of pulsed and continuous waves.

The high and low voltage controllers 20, 22 includes transistors, gate drivers or other devices for receiving inputs and controlling the high voltage switches 12, 14 and low voltage switches 16, 18 in response to inputs. For example, an enable signal is provided on the enable input 36 for allowing the operation of the controllers 20, 22. A mode signal input on the mode input 32 indicates whether the high voltage switches 12, 14 are to be operated for a pulsed wave mode or the low voltage switches 16, 18 in a continuous wave mode. After enabling the controllers 20, 22 and configuring the controllers 20, 22 for operation pursuant to the desired mode, one or both of the controllers 20, 22 is responsive to the pulse signal on timing input 34 for generating a single one or a sequence of pulses. FIG. 3 shows a table of states of the high voltage switches 12, 14 and low voltage switches 16, 18 in response to the enable, mode and pulsing input signals. During continuous wave operation, the high voltage controller 20 maintains the state of the high voltage switches 12, 14, and the low voltage controller 22 causes the low voltage switches 16, 18 to alternate states. During pulse wave operation, the low voltage controller 22 causes the low voltage switches 16, 18 to maintain a state, and the high voltage controller 20 causes the high voltage switches 12, 14 to alternate states. Additional, different or fewer controls may be provided. For example, the powered down mode may be associated with all of the switches 12-18 in an off state. The controls are all low voltage CMOS inputs, such as 5 volt inputs, but other voltage levels or multiple voltage levels may be used.

The voltage provided at the low voltage input 30 and the high voltage input 28 is supplied by fixed or variable voltage sources. Other voltage regulators may be provided, such as providing for a voltage supply or regulation integrated within the integrated circuit 10.

Figure 2:
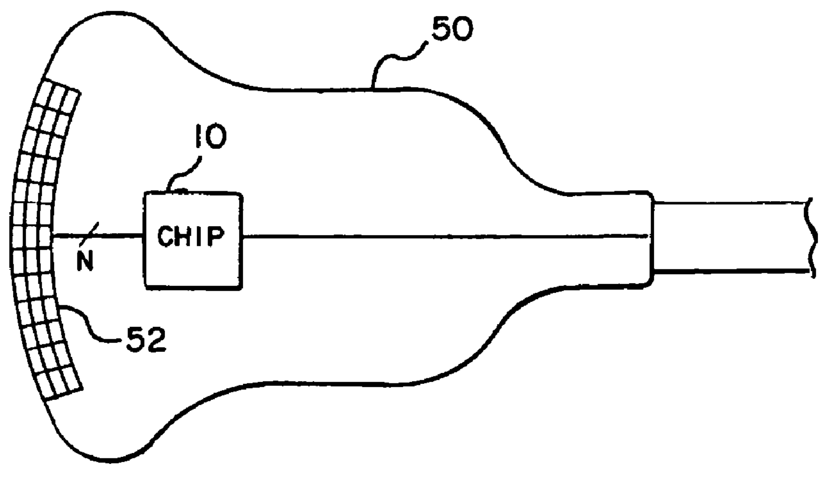
FIG. 2 is a cross-sectional diagram of one embodiment of a transducer incorporating the integrated circuit of FIG. 1.

The integrated circuit 10 is used within an ultrasound system. For example, a coaxial cable connects the common output 24 to a transducer element of an ultrasound array. In another embodiment shown in FIG. 2, the integrated circuit 10 is positioned within a transducer housing 50 for connection to a multi-dimensional array 52. The common output 24 connects with one or more elements of the array 52. By integrating both high and low voltage switches in the same integrated circuit 10, continuous and pulsed wave operation may be provided with lesser power dissipation. By operating only low voltage switches 16, 18 for continuous wave operation, less power is consumed. Less power consumption results in a lesser generation of heat. Similarly less power dissipation may be desired for use with battery operated or other restricted power supplies. The relationship between continuous wave and pulsed wave power dissipation of a single pulser is roughly defined by $P_{pw}/P_{cw}=(V_{pp}^2 DF_{pw})/(V_{cw}^2)$ where $DF_{pw}$ is the duty factor for the pulse waveform mode, $V_{pp}$ is the high power voltage and $V_{cw}$ is the low power voltage. The duty factor for the pulse wave mode ranges between 0.1% and 1%. For a high voltage of 200 volts and a low voltage of 12 volts, the ratio of the pulsed waveform to the continuous waveform powers is between 0.28 and 2.8. The continuous wave power dissipation is reduced to the range of the pulsed wave power dissipation. Since continuous wave operation is associated with some elements operating on transmit and others operating on receive at a same time, a continuous wave aperture may be less than a pulse wave aperture. As a result, the reduction in size of the continuous wave transmit aperture also provides a reduction in power dissipation.

As compared to operation with just the pulsed wave components, the integrated circuit 10 provides for continuous wave operation with an input for the mode 32 and the low voltage input 30. Both the mode and the low voltage inputs 30, 32 are common to a plurality of pulsers for use with the array 52 of elements. Additional per channel interconnections are accordingly limited. As a result, the board space and trace routing requirements for a plurality of application specific integrated circuits each implementing a plurality of transmitters and associated waveform generators is simplified. Since the high voltage switch 14 and low voltage switch 18 are used for protecting the low voltage switches 16 and 18 from the high voltage input 28 and for connecting the high voltage switch 14 to ground while sharing a common output, the circuit requirements may be reduced. For example, the common output 24 connects directly to the transducer elements without further integrated or external components for selecting between the two different types of pulsers.

FIG. 4 shows one embodiment of a method for generating transmit waveforms as either of pulsed and continuous waves from a same chip or integrated circuit. The method uses the integrated circuit 10 shown in FIG. 1 or FIG. 2, but other integrated circuits, chips, transmitters, waveform generators or devices may be used. Additional, different or fewer acts than shown in FIG. 4 may be provided.

In act 60, connections are made for generating pulsed waves. A low, ground or substantially zero voltage is connected to a high voltage switch with a low voltage switch. A common output connects directly to one or more of the high voltage switches. Both the high voltage and low voltage switches are integrated within a same integrated circuit and semiconductor chip. In alternative embodiments, two or more high voltage switches are connected to the low, zero or ground voltage and/or two or more low voltage switches are used to provide the connection.

In act 62, connections are performed for generating continuous waves. An output used for outputting both continuous and pulsed waves is connected to low voltage switches. One or more high voltage switches are used to perform the connection. Another high voltage switch isolates the low voltage switches from the high voltage source.

In act 64, pulsed waves are generated with the high voltage switches in the integrated circuit. For example, the common output is switched between a high voltage source and a ground or substantially constant lower voltage. As another example, the common output is switched between a high positive voltage source and a high negative voltage source. During generation of the pulsed waveforms, one or more of the low voltage switches connects one or more of the high voltage switches to ground or other low voltage.

In act 66, continuous waves are generated with low voltage switches in the integrated circuit. The common output is switched between the low voltage source and ground. As another example, the low voltage switches are switched between positive and negative low voltages. The resulting continuous wave is provided on an output common with or the same as used for pulse wave generation. During continuous wave operation, one or more of the high voltage switches connects the low voltage switches to the common output.

In act 68, the pulse waves are output when generated, and the continuous waves are output when generated. Continuous and pulsed waves are generated at different times but share a common output from the same integrated circuit and associated semiconductor chip. The same transmitter and associated waveform generator may be used for generating either pulsed waves or continuous waves for different modes of ultrasound imaging.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. In a transmitter for ultrasound imaging with pulsed wave and continuous wave operation, an improvement comprising:

high and low voltage switches integrated on a same circuit and having a common output from the circuit, wherein the high voltage switches comprise a pulse wave pulser operable to generate pulsed waves on the common output while the low voltage switches are maintained in a steady state, and wherein the low voltage switches comprise a continuous wave pulser operable to generate continuous waves on the common output while the high voltage switches are maintained in the steady state;

wherein the circuit comprises a semiconductor chip, the common output being an output of the semiconductor chip.

2. The transmitter of claim 1 wherein the common output is directly connected with at least one of the high and low voltage switches.

3. The transmitter of claim 1 wherein a first high voltage switch connects between a high voltage input and the common output, a second high voltage switch connects between the common output and a first low voltage switch, the first low voltage switch connecting between the second high voltage switch and a low voltage input, and a second low voltage switch connected between the first low voltage switch and a ground or additional connector.

4. The transmitter of claim 3 wherein, during the pulsed wave operation, the second low voltage switch is closed, the first low voltage switch is open and the first and second high voltage switches alternate states.

5. The transmitter of claim 3 wherein, during the continuous wave operation, the first high voltage switch is open, the second high voltage switch is closed and the first and second low voltage switches alternate states.

6. The transmitter of claim 1 wherein the high voltage switch comprises a first transistor having a threshold greater than 6 volts and being operative with at least 10 volts and wherein the low voltage switch comprises a second transistor having a threshold voltage less than 6 volts and being smaller than the first transistor.

7. The transmitter of claim 1 wherein the low voltage switch is operable to provide a first low resistance path from the high voltage switch to ground during the pulsed wave operation and wherein the high voltage switch is operable to provide a second low resistance path from the low voltage switch to the common output during the continuous wave operation.

8. The transmitter of claim 1 wherein a first resistance from a first drain to a first source in an on state of the low voltage switch is at least half a second resistance from a second drain to a second source in an on state of the high voltage switch.

9. The transmitter of claim 1 wherein the transmitter connects with a multi-dimensional array of elements in a transducer housing, the transmitter within the transducer housing.

10. The transmitter of claim 1 further comprising:

separate high and low voltage power supply connectors, the high voltage power supply connector connected with the high voltage switch and the low voltage power supply connector connected with the low voltage switch.

11. The transmitter of claim 1 further comprising:

first and second controllers operable to control the high and low voltage switches, the first and second controllers operating in response to low voltage CMOS logical inputs.

12. A waveform generator for ultrasound imaging, the waveform generator comprising:

a chip;

at least a first higher voltage switch integrated in the chip;

at least a first lower voltage switch integrated in the chip with the first higher voltage switch; and an output of the chip, the output connected with the first higher voltage switch and the first lower voltage switch such that the first higher voltage switch outputs to the output in a first mode and the first lower voltage switch outputs to the output in another mode.

13. The waveform generator of claim 12 wherein the chip comprises an integrated circuit having the at least first higher and lower voltage switches.

14. The waveform generator of claim 12 wherein the output is directly connected with at least one of the higher and lower voltage switches.

15. The waveform generator of claim 12 wherein the at least a first lower voltage switch comprises the first lower voltage switch and a second lower voltage switch, the at least a first higher voltage switch comprises the first higher voltage switch and a second higher voltage switch, the first higher voltage switch connecting between a high voltage input and the output, the second higher voltage switch connecting between the output and the first and second lower voltage switches, the first lower voltage switch connecting between the second higher voltage switch and a low voltage input, and the second lower voltage switch connecting between the first low voltage switch and a ground or additional connector.

16. The waveform generator of claim 12 further comprising a first controller connected with the first higher voltage switch and a second controller connected with the first lower voltage switch, the first controller operable to maintain a state of the first higher voltage switch and the second controller operable to alternate states of the first lower voltage switch during said another mode comprising continuous wave operation, and the first controller operable to alternate states of the first higher voltage switch and the second controller operable to maintain a state of the first lower voltage switch during said first mode comprising pulsed wave operation.

17. The waveform generator of claim 12 wherein the first higher voltage switch comprises a first transistor having a threshold greater than 6 volts and being operative with at least 10 volts and wherein the first lower voltage switch comprises a second transistor having a threshold voltage less than 6 volts and being smaller than the first transistor.

18. The waveform generator of claim 12 wherein the first lower voltage switch is operable to provide a first low resistance path from the first higher voltage switch to ground during said first mode comprising pulsed wave operation and wherein the first higher voltage switch is operable to provide a second low resistance path from the first lower voltage switch to the output during said another mode comprising continuous wave operation.

19. The waveform generator of claim 12 wherein a first resistance from a first drain to a first source in an on state of the first lower voltage switch is at least half a second resistance from a second drain to a second source in an on state of the first higher voltage switch.

20. The waveform generator of claim 12 further comprising:

a transducer housing; and a multi-dimensional array of elements within the transducer housing;

wherein the output connects with the multi-dimensional array of elements in the transducer housing, the waveform generator also within the transducer housing.

21. A method for generating a transmit waveform as either of pulsed and continuous waves, the method comprising:

generating pulsed waves with high voltage switches in an integrated circuit;

generating continuous waves with low voltage switches in the integrated circuit;

connecting a low or zero voltage to at least one of the high voltage switches with at least one of the low voltage switches during generation of the pulsed waves; and outputting the pulsed waves when generated and the continuous waves when generated on a common output from the integrated circuit.

22. The method of claim 21 further comprising:

connecting the common output to the low voltage switches with at least one of the high voltage switches when generating the continuous waves.

23. The method of claim 21 wherein outputting comprises outputting the pulsed or continuous waves from the common output on a semiconductor chip of the integrated circuit.

24. The method of claim 21 wherein generating pulsed waves comprises switching the common output between a high voltage source and ground, one of the low voltage switches connecting one of the high voltage switches to the ground.

25. The method of claim 21 wherein generating continuous waves comprises switching the common output between a low voltage source and ground, one of the high voltage switches connecting the low voltage switches to the common output.

26. The method of claim 21 further comprising:

connecting a connector to the high voltage switches when the pulsed waves are generated and connecting the connector to the low voltage switches when the continuous waves are generated, the connector operable to receive electric signals generated in response to acoustic echoes.

* * * * *